United States Patent
Gutman

(10) Patent No.: US 7,120,224 B2
(45) Date of Patent: Oct. 10, 2006

(54) X-RAY IMAGING APPARATUS AND METHOD FOR MAMMOGRAPHY AND COMPUTED TOMOGRAPHY

(75) Inventor: George Gutman, Birmingham, MI (US)

(73) Assignee: Advanced X-Ray Technology, Inc., Birmingham, MI (US)

( * ) Notice: Subject to any disclaimer, the term of this patent is extended or adjusted under 35 U.S.C. 154(b) by 0 days.

(21) Appl. No.: 11/258,261

(22) Filed: Oct. 25, 2005

(65) Prior Publication Data

US 2006/0093084 A1 May 4, 2006

Related U.S. Application Data

(60) Provisional application No. 60/624,411, filed on Nov. 2, 2004.

(51) Int. Cl.
*A61B 6/04* (2006.01)
(52) U.S. Cl. .......................................... 378/37; 378/147
(58) Field of Classification Search .................. 378/37, 378/65, 64, 84, 147, 145, 85, 62, 57, 51
See application file for complete search history.

(56) References Cited

U.S. PATENT DOCUMENTS

| | | |
|---|---|---|
| 6,480,566 B1 | 11/2002 | Muller |
| 6,580,940 B1 | 6/2003 | Gutman |
| 2002/0003856 A1* | 1/2002 | Gutman ........................ 378/65 |
| 2002/0014591 A1* | 2/2002 | Ghelmansarai ............. 250/366 |

* cited by examiner

*Primary Examiner*—Edward J. Glick
*Assistant Examiner*—Hoon Song
(74) *Attorney, Agent, or Firm*—Brooks Kushman P.C.

(57) ABSTRACT

An x-ray imaging apparatus for mammography. The apparatus places the focal spot of the x-ray source as close as possible to a compression paddle or into a desired region of tissue. The apparatus comprises an x-ray source, a collimator with conditioning optics which focus and direct x-ray radiation to a metal pseudo-target in the collimator or a needle placed along the x-ray beam, paddles for breast compression and a detector. The pseudo-target re-emits monochromatic x-ray radiation with an energy, intensity, and space distribution that are adjustable in accordance with a desired imaging procedure.

20 Claims, 6 Drawing Sheets

14 – DIAPHRAGM (SHUTTER)

15 - NEEDLE
16 - SEMITRANSPARENT MOLYBDENUM PLATE
17 - COMPRESSION PADDLE WITH HOLE

X-RAY IMAGING APPARATUS AND METHOD FOR MAMMOGRAPHY AND COMPUTED TOMOGRAPHY

CROSS-REFERENCE TO RELATED APPLICATION

This application claims the benefit of U.S. provisional application Ser. No. 60/624,411, filed Nov. 2, 2004, which is incorporated herein by reference.

BACKGROUND OF THE INVENTION

1. Field of the Invention

The present invention relates to an x-ray apparatus for medical radiology. More specifically, the invention relates to an x-ray apparatus for mammography, including receiving tomosynthesis data and obtaining radiological images in galactography (see, e.g., U.S. Pat. No. 6,480,566 which is incorporated by reference herein) and angiography. This invention also can be used in computer tomography.

2. Background Art

Mammography is a tool for diagnosing breast cancer. Images of a tumor can be viewed on film or (if it is used a digital detector) on a computer screen. Successful treatment of breast cancer depends on early diagnosis. Mammography plays a central part in early detection because it can show changes in the breast up to two years before a patient or physician can feel them. Due to mammography in the United States, the death rate from breast cancer has dropped almost 20% in the past decade, after having been stable for the prior 50 years (Nass, SJ et al, Mammography and Beyond: Developing Technologies For the Early Detection of Breast Cancer, National Academy, pp. 18–19, 2001).

X-ray apparatus for mammography currently exists. It has a typical distance of about 65 cm between the focal spot of an x-ray source and a top paddle. In mammography, the physician would like to have the focal spot of the x-ray source as close as possible to the sternum of a patient to be examined, and thus over the free end—representing the exposure side of the x-ray examination system—of a support provided for the breast of the patient. This permits irradiation of the tissue to be examined as completely as possible, since the x-rays emanate from the focal spot and include the base of the breast, i.e., that region of the breast that forms the transition to the rib cage.

There is also a desire in computed tomography to have the exposure plane, i.e., the plane of the body layer to be exposed, and thus the focal spot of the x-ray source, as close as possible to the actuation side of a gantry, i.e., that side of the gantry at which the physician is located for preparation of the exposure and possibly during examination. The actuation side of the gantry is usually provided with control and/or display elements.

Although mammographic screening for breast cancer has proved invaluable in the early detection and diagnosis of breast cancer, conventional mammography does not detect all cancers. As many as 20% of the cancers that become evident during one year would not have been visible at screening mammography procedures performed within that year. A major factor contributing to this situation is the "structured noise" created by the overlap of normal structures, which are superimposed on each other in the acquisition of a two-dimensional mammographic projection. This recognition has prompted recent interest in breast tomosynthesis. Breast tomosynthesis acquires multiple images as the x-ray source moves through an arc above the stationary compressed breast and digital imaging detectors. In turn, this creates a need for a monochromatic, easily movable, small size, x-ray source which can be placed in close proximity to the examined tissue.

There exists an x-ray apparatus, including an x-ray source, which can be placed above a top paddle or even implanted into a patient's body for directly irradiating a desired region of tissue with the x-rays (e.g., U.S. Pat. No. 6,580,940 issued to G. Gutman, which is incorporated by reference). That apparatus delivers monochromatic, low energy x-ray radiation to the examined tissue from an easily movable, small size focus x-ray source.

SUMMARY OF THE INVENTION

Thus, it is an object of the present invention to provide an apparatus with a movable, monochromatic, small size, point x-ray secondary source that is movable and can effectively irradiate the tissue to be examined.

Another object of the invention is to provide an x-ray imaging apparatus for mammography that transforms the primary focal spot of the x-ray tube by using a collimator with capillary focusing optics that create a focused beam.

It is a further an object of the invention to provide an imaging apparatus with means for monochromatization of the incident x-ray beam by using a secondary target for absorbing the incident x-ray beam and re-emitting monoenergetic (monochromatic) fluorescent x-rays from the focal spot of the secondary target through means for shaping the re-emitted beam.

It is also an object of the invention to provide an imaging apparatus that effectively moves the focal spot of the secondary target re-emitting a monochromatic x-ray beam close to the compression paddle of the apparatus, or directly to a desired region of tissue.

It is yet another object of the invention is to provide the imaging apparatus with a collimator having means for moving the secondary target along the optical axis by a controlled, precisely-defined distance.

It is yet a further object of the invention is to provide the imaging apparatus with means for smoothly moving a primary x-ray source (x-ray tube) and collimator with a secondary target with particular reference to orthogonal collimator with a secondary target with particular reference to orthogonal coordinates through pre-defined positions.

The ability to place the secondary target at any desirable point allows one to obtain x-ray images of the patient's tissue from different angles. These images can then be processed for reconstruction of a 3D image.

Briefly, the present invention includes a primary x-ray source (x-ray tube) of adjustable intensity for creating x-ray radiation, a collimator with focusing optics and a secondary target. The x-ray tube is conjugated with the collimator. An output window is provided in an end region of the collimator. The collimator end with a secondary target may be positioned just above a compression paddle or in a patient's body to irradiate a desired region with x-rays.

The x-ray apparatus includes means for smoothly moving the primary x-ray source and the collimator with the secondary target as a unit. In one embodiment, the collimator also has means for movement of the secondary target with a semilens along the optical axis by a defined distance.

The output window is made of an x-ray transparent material. The shape and the energy of fluorescent x-rays emitted from the secondary target can be changed by changing the material of the secondary target (e.g. a metallic material) and the shape of the window.

The disclosed x-ray imaging apparatus allows one to move a monochromatic, x-ray point source (secondary target) through a plurality of pre-defined positions relative to a stationary film, plate or other detector (collectively "detector") and a patient's breast to obtain various x-ray images that can be transformed, if desired, into 3D images.

The disclosed invention can be also used for obtaining radiological images in computer tomography, galactography, angiography and other diagnostic applications.

DETAILED DESCRIPTION OF THE PREFERRED EMBODIMENT(S)

1. The Apparatus

Figure 1:
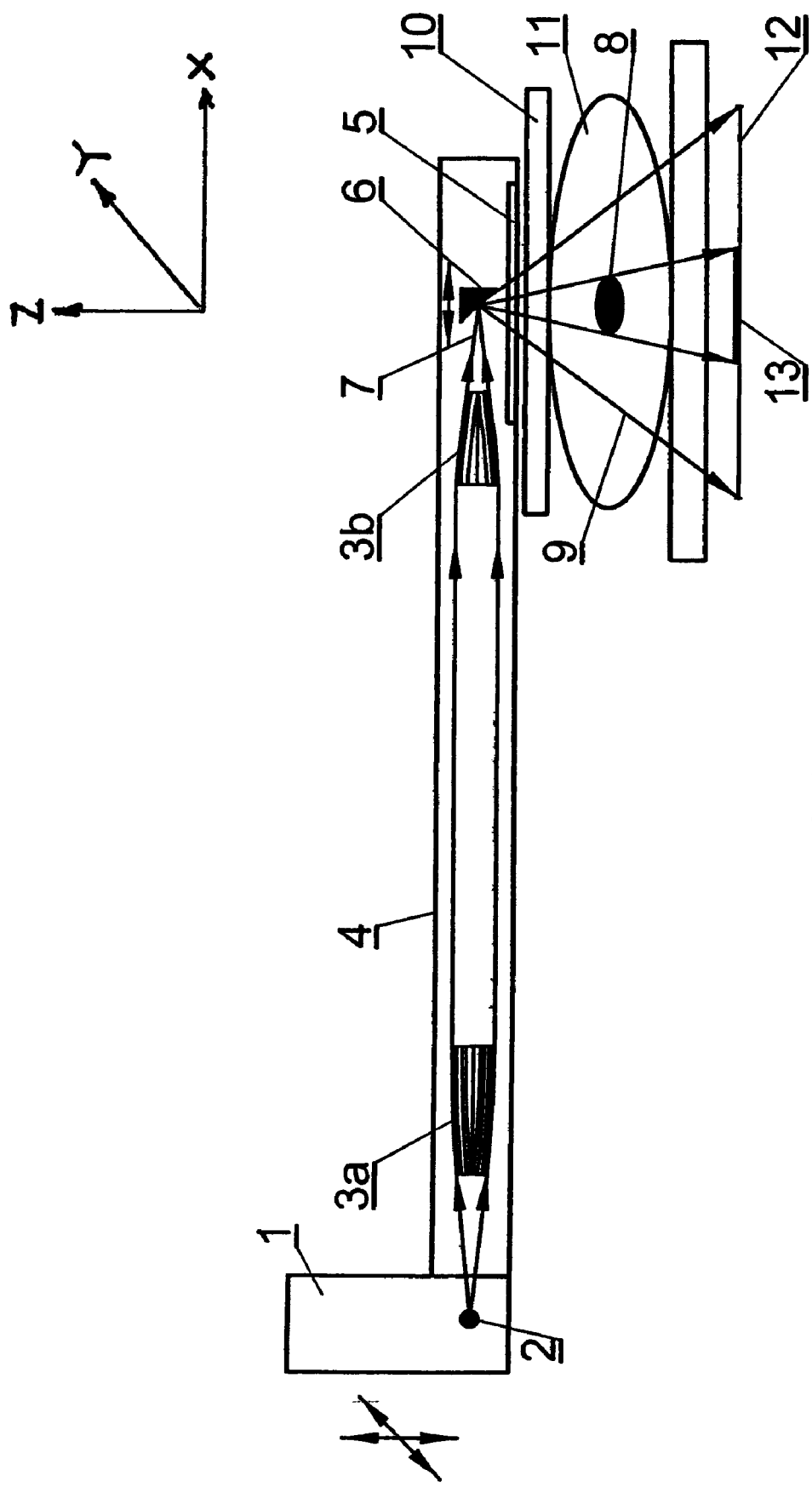
FIG. 1 is a schematic representation of a system showing an x-ray source, a collimator, secondary pseudo-target and a detector.

FIG. 1 shows one embodiment of an x-ray imaging apparatus for mammography. The apparatus has: an x-ray source 1 (x-ray tube with a Rh or Ag anode) with a point focus 2 and a capillary lens, means for shaping, or preferably two semilenses 3a and 3b within a collimator 4 (attached to the x-ray tube 1). The collimator has an output window 5 and a secondary or pseudo-target 6. The pseudo-target 6 or means for monochromatizing is preferably made from a metallic material such as Mo that allows two-stage production of monochromatic x-ray radiation with the highest effectiveness.

First, a primary x-ray beam 7 generated by an x-ray tube 1 is guided towards the secondary target 6 through the collimator 4. The primary x-ray beam 7 excites the pseudo-target 6 and causes the target to emit x-ray fluorescence that is mainly defined by the characteristic lines of the target material and the parameters of the incident x-ray beam. At least part of the re-emitted fluorescent radiation 9 penetrates the compression paddle 10 and a compressed tissue 11. It creates an image 13 of a tumor 8, the image being projected on an x-ray film 12, on a digital detector, or other receiving and recording medium (collectively "detector").

To achieve high spatial resolution and maximum contrast between the soft tissue components in the breast, a low energy x-ray must be used. The choice of x-ray energy in mammography is a compromise between dose and contrast resolution. X-ray radiation below 15 keV contributes mainly to radiation dose and should be excluded. X-ray radiation above 25 keV contributes mainly to the noise and decreases the contrast. The "useful" x-ray spectrum (about 15–25 keV) may be achieved by using different approaches. A monochromatic x-ray source gives the best results.

The changing of x-ray intensity obeys an inverse square ($R^2$) law, where R is the distance from the pseudo-target 6 to the image. When the energy of the incident beam (22.2 keV and 20.2 keV for an x-ray tube with Ag and Rh anode respectively) is equal to or slightly above the absorption edge of the pseudo-target material (Mo absorption edge is 20.0 KeV), the conversion efficiency of the excitation energy into x-ray fluorescence is optimal.

Thus, this arrangement enables the disclosed apparatus to create images of tumors, and mammograms in particular.

The x-ray apparatus uses a focused x-ray beam 7 that is delivered through capillary lenses 3a and 3b that are optically conjugated with the focus 2 of the x-ray tube 1. The pseudo-target 6 mechanically connects with semilens 3b.

FIG. 1 depicts for reference the axes X, Y, and Z. Imagine that the paddle 10 lies in the X-Y plane. The pseudo-target 6 and semilens 3b can move as a unit along the collimator 4 (along the X-axis), while the focus of the x-ray beam 7 remains on the pseudo-target 6. The position of the point focus of the secondary x-ray source will change, thereby producing the tumor's image from different angles.

Under the influence of means for moving (such as an electrically-driven system that rides along a track or rails), the collimator 4 and x-ray tube 1 can move as a unit along the Y-axis in the X-Y plane and along the Z-axis, perpendicular to the X-Y plane. By moving the assembly containing the x-ray tube 1 with a mechanically coupled collimator 4 and the pseudo-target 6 parallel to the surface (i.e., parallel to the X-Y plane) of the compression paddle 10 and in a direction perpendicular to the compression paddle (along the Z-axis) relative to a stationary detector 13 and a patient's breast 11, a variety of x-ray images of the patient's tumor can be produced. These can then be processed for examination or used to construct a 3D image.

The output window 5 is substantially transparent to x-rays (e.g., for the fluorescent line of a Mo pseudo-target of 17.5 keV, more than 98% of incident x-rays pass through).

An x-ray tube that is used as an x-ray source can have a point or a linear focus. For a linear focus, a take-off angle is chosen so that the projection of the linear focus onto a plane perpendicular to the optical axis of the x-ray system is a point.

Thus, the invention includes means for transferring the focal spot of the x-ray tube to the compression paddle of the imaging apparatus for mammography. Conditioning optics, capillary optics in particular, are incorporated into the collimator to provide a high intensity focusing x-ray beam. The apparatus delivers radiation to the pseudo-target which, in turn, absorbs the incident beam and re-emits fluorescent monochromatic x-ray radiation in a hemispherical pattern.

Figure 2:
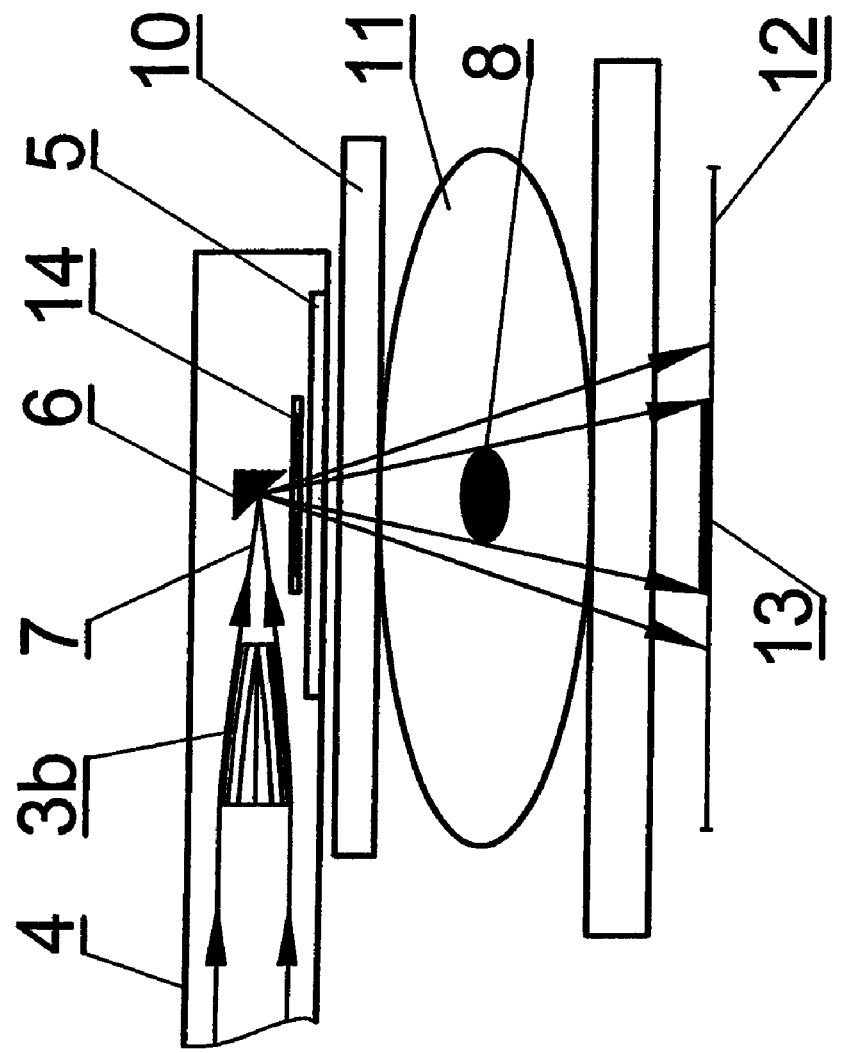
FIG. 2 is a schematic representation of an end region of the collimator with a window and a diaphragm having a changeable aperture.

FIG. 2 shows an end region of the collimator 4 with a semilens 3b and pseudo-target 6. The window 5 is provided with a diaphragm (shutter) 14. The opening size of the diaphragm can change the irradiated area of a breast, thereby minimizing the dose delivered to surrounding healthy tissue. As mentioned earlier, semilens 3b and the pseudo-target 6 are mechanically connected so that they may move in unison relative to the collimator 4. If desired, the diaphragm 14 can move relative to the collimator 4, thereby ensuring irradiation of the tumor 8. In a preferred embodiment, the collimator comprises two capillary semilenses 3a, 3b. This approach de-magnifies the focus spot on the pseudo-target.

In one form, each capillary lens subassembly includes a plurality or band of capillaries having a complex curvature. They capture a divergent beam that is produced by the primary x-ray source and transforms it first into a parallel beam, and then a focused one with a high intensity. In capillary optics-based collimation, x-rays incident on the interior of a narrow capillary at small angles (less than the critical angle for total external reflection) are guided down the tubes by total internal reflection. By assembling a large number of hollow capillary tubes, a special arrangement can be formed. Kumakhov M A, "Capillary X-Ray Optics—Introduction", Nuclear Instruments and Methods, B48, 283–9 (1990). See, also, Arkd'evVA et al., "New Components For X-Ray Optics", Sov. Phys. USP 32, 271–6 (1989). Each of these publications is incorporated herein by reference.

Figure 3:
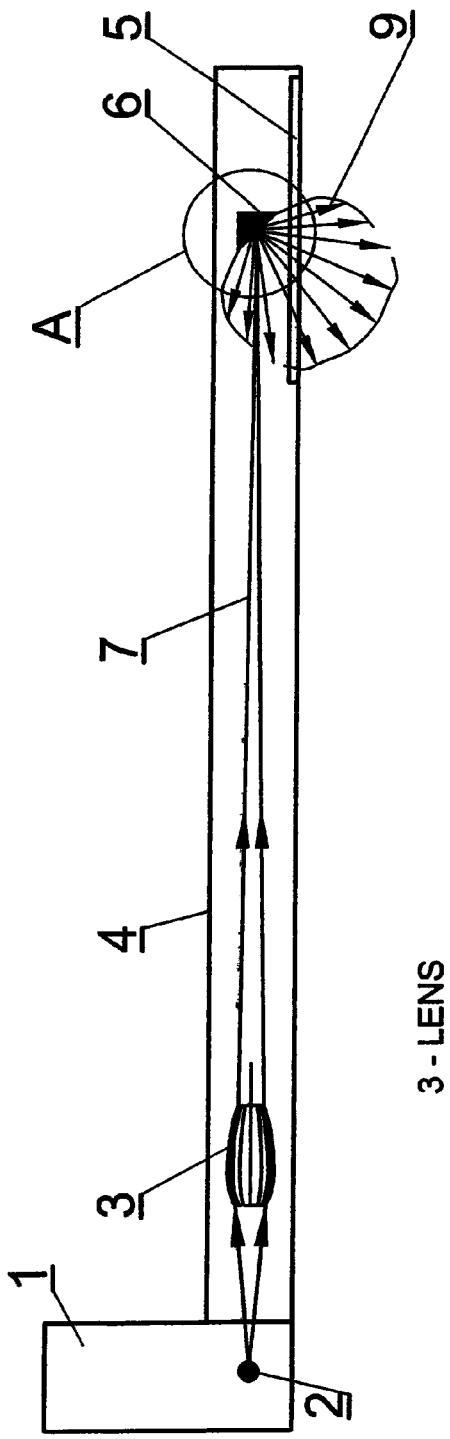
FIG. 3 is a schematic representation of the collimator with one long-focus capillary lens, and a quasi-parallel beam created thereby.
Figure 3:
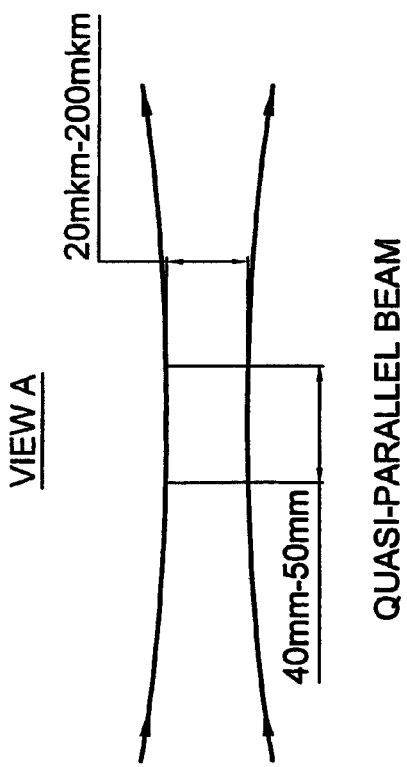

In an alternative embodiment (FIG. 3) only one focusing capillary lens 3 with a long (preferably 40–50 mm length) focus is used. Such an approach increases the intensity of x-rays incident on the pseudo-target (one lens instead of two lenses) but limits the distance of a pseudo-target translation.

Figure 4A:
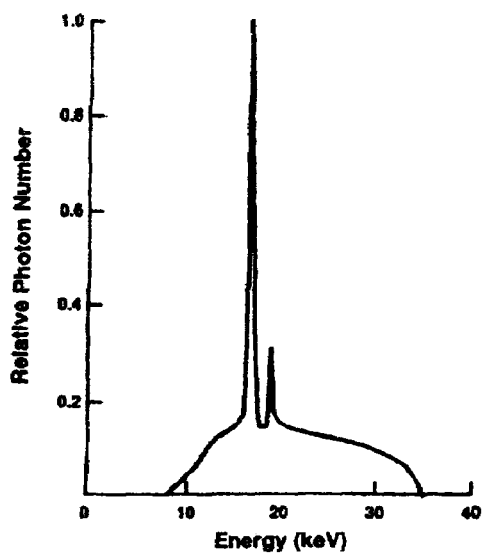
FIG. 4a is an x-ray emission spectrum for a Mo target x-ray tube operated at 35 keV.

In conventional mammography, an x-ray tube usually is used with a Mo anode (Ka line 17.5 keV) operating at U=35–40 keV. An x-ray emission spectrum for a Mo-target x-ray tube operated at 35 keV is shown in FIG. 4a. Only the central part of the spectrum (from about 16 keV to 20 keV) "participates" in the creation of an x-ray image of a tumor. Low energy x-rays (below 16 keV) are mainly responsible for undesired dosage. High energy x-rays (from 20 keV to 35 keV) create undesired scattering. This dramatically decreases the contrast of an x-ray image.

Figure 4B:
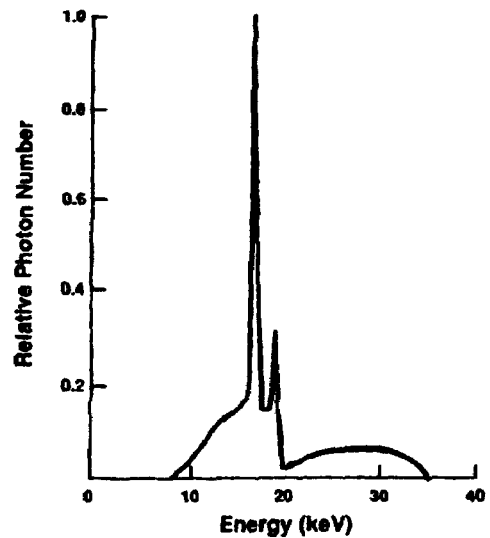
FIG. 4b is an x-ray emission spectrum for a Mo target x-ray tube with a Mo filter operated at 35 keV.

To improve contrast, an additional Mo filter is used (FIG. 4b). However, undesirable radiation results.

Figure 4C:
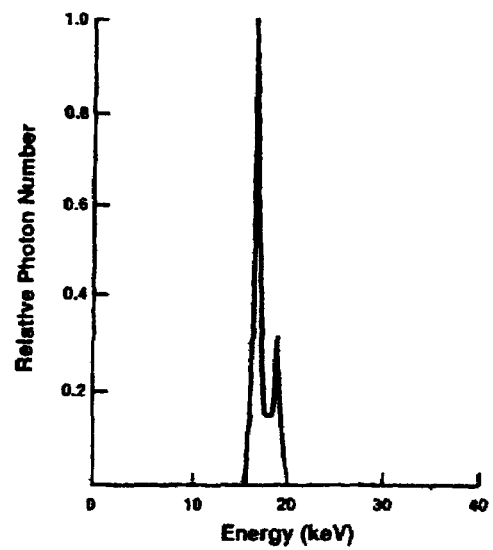
FIG. 4c is an x-ray emission spectrum from a Mo pseudo-target irradiated by x-rays emitted from an x-ray tube with an Ag anode.

The spectrum of fluorescent radiation emitted from a Mo pseudo-target (shown in FIG. 4c) improves the image's contrast and decreases undesirable absorbed dosage.

Figure 5:
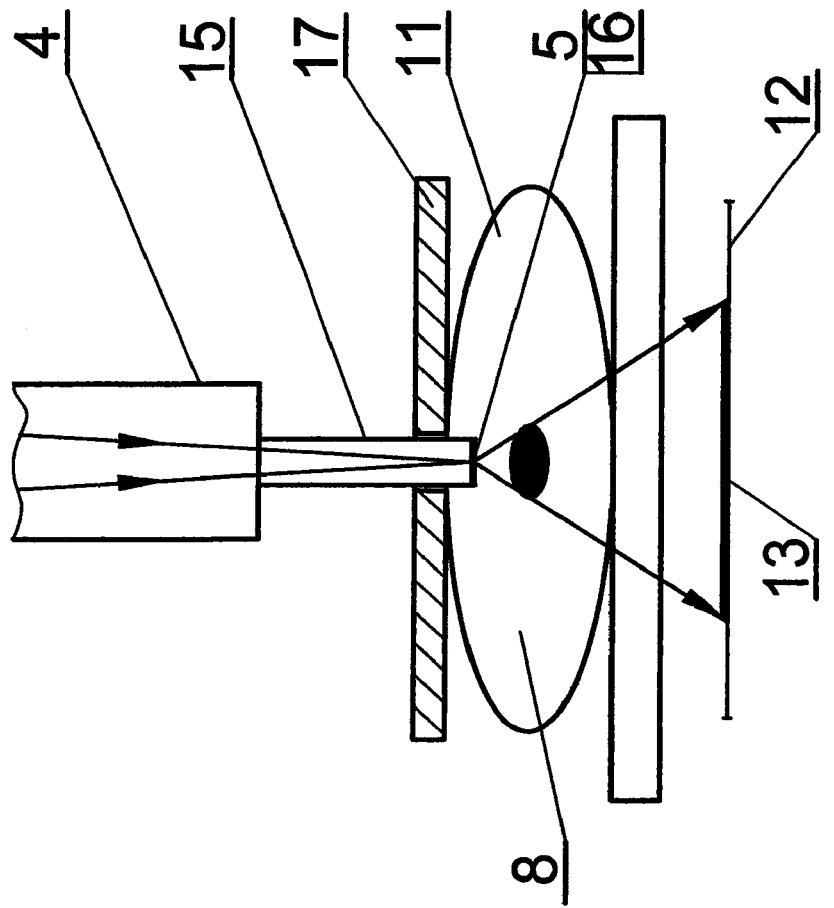
FIG. 5 is a schematic representation of a system for delivering a psuedo-target inside the site to be investigated.

In special cases, e.g., when one cannot reliably interpret the image received from a conventional mammogram, the pseudo-target can be placed close in proximity to or inside the site to be analyzed (e.g., a breast) in the area under investigation (e.g., a tumor, FIG. 5). This approach dramatically increases the magnification and contrast of the image, while minimizing the delivered dosage. In this embodiment (FIG. 5) the collimator 4 is provided with a needle 15, window 5, and a semitransparent, thin Mo plate 16. The compression paddle 17 is provided with a hole that allows placement of the needle in the desired position to receive an optimal image of investigating area. An x-ray beam is focused on the semitransparent pseudo-target 16, which is preferably less than 50 microns thick. The x-ray fluorescence emitted by the semitransparent pseudo-target 16 irradiates the area of interest, thereby creating an image 13 on the film 12.

Figure 6:
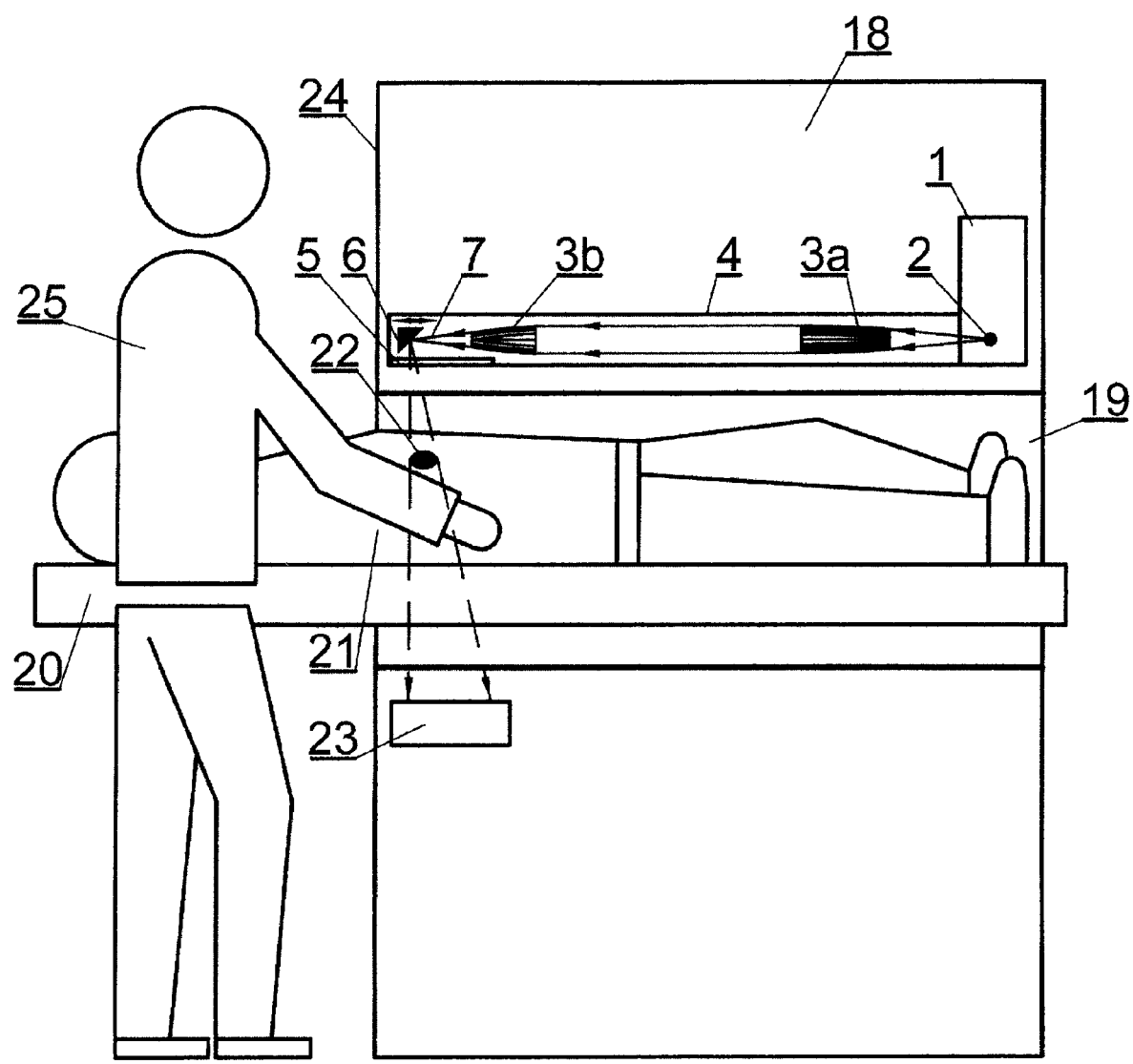
FIG. 6 is a schematic representation of the environment in which the invention is used including a gantry, illustrating its position in relation to the patient and the physician.

It was noted earlier that there is a desire in computed tomography to have the exposure plane, i.e., the plane of the body layer to be exposed, and thus the focal spot of the x-ray source to be as close as possible to the actuation side of a gantry, i.e., that side of the gantry at which the physician is located for the preparation of the exposure and possibly during examination. FIG. 6 illustrates these points. In that figure, the inventive x-ray imaging apparatus for computed tomography includes a gantry 18 in which the x-ray tube 1 has a collimator 4 and a psuedo-target 6 that are mounted so as to be rotatable around an opening 19 of the gantry 18. Illustrating further the environment in which the invention is used, a support table 18 for a patient 21 extends through the opening 19 so that a region 22 of interest in the patient 21 can be examined. Thus, as noted earlier, the inventive apparatus allows the pseudo-target 6 to lie very close to the actuation site 24 of the gantry 18, so that the patient is more easily accessible to the physician 25.

2. The Method

The methodology of developing and using the disclosed x-ray imaging apparatus involves:

1. designing, fabricating and testing conditioning (e.g. capillary) optics;
2. incorporating such conditioning optics into an optical collimator;
3. conjugating the collimator with an x-ray source; and
4. carrying out experiments to characterize the exposure required for creating an image of the highest quality, while minimizing the dosage delivered to the irradiated tissue.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. An x-ray imaging apparatus for mammography, the apparatus comprising:
   a primary x-ray source for generating x-ray radiation;
   a collimator with capillary optics which direct and focus the x-ray radiation, the collimator being in optical communication with the primary x-ray source;
   means for monochromatizing the radiation positioned within the collimator;
   means for shaping the radiation, positioned within the capillary optics;
   an optically transparent paddle for supporting an anatomical site of interest while allowing the passage of x-ray radiation; and
   means for registering an image of the anatomical site, the apparatus thereby delivering monochromatic x-rays with a suitable energy, intensity, and space distribution and transforming the focal spot of the x-ray tube to a position in close proximity to a compression paddle, or directly to a desired region of tissue, the characteristics of the x-rays being adjustable in accordance with a desired imaging procedure.

2. The x-ray apparatus according to claim 1, wherein the means for shaping include focusing optics that de-magnify the focal spot size of the primary x-ray source.

3. The x-ray apparatus according to claim 1, wherein the means for monochromatizing includes a secondary target for absorbing an incident x-ray beam and re-emitting monochromatic fluorescent x-rays, the x-rays emanating from a focal spot of the secondary target.

4. The x-ray apparatus according to claim 3, wherein the secondary target comprises a metallic material.

5. The x-ray apparatus according to claim 3, wherein the collimator includes means for moving the secondary target along an optical axis by a defined distance.

6. The x-ray apparatus according to claim 3, wherein the collimator includes means for moving the secondary target and an associated semilens in unison, thereby defining the position of the focus of the irradiated beam on the pseudo-target.

7. The x-ray apparatus according to claim 3, wherein the collimator is provided with a window that is transparent to x-ray radiation and with a diaphragm having a changeable aperture that minimizes the dosage delivered to healthy tissue.

8. The x-ray apparatus according to claim 3, wherein the apparatus includes means for moving the primary x-ray source and the collimator in unison with the secondary target through pre-defined positions to obtain a plurality of x-ray images of the anatomical site which is processed for examination or used to construct a 3D image.

9. The x-ray apparatus according to claim 3, wherein the means for shaping include conditioning optics with one or more capillary lenses to condition the radiation in a region from about 10 keV to 30 keV.

10. The x-ray apparatus according to claim 3, wherein an x-ray beam emitted from the primary x-ray source has an energy which is equal to or slightly above the absorption edge of the means for monochromatizing so that the conversion efficiency of the excitation energy into x-ray fluorescence is optimal.

11. The x-ray apparatus of claim 10, wherein the average energy of the incident beam is about 22.2 keV when the x-ray tube has an Ag anode.

12. The x-ray apparatus of claim 10, wherein the average energy of the incident beam is about 20.2 keV when the x-ray tube has an Rh anode.

13. The x-ray apparatus according to claim 3, further including means for moving the collimator and the x-ray tube as a unit along Y-axis in an X-Y plane and along a Z-axis, perpendicular to the X-Y plane.

14. The x-ray apparatus according to claim 7, wherein the window allows more than 98% of incident x-rays to pass through for a fluorescent line of a Mo pseudo-target of 17.5 keV.

15. The x-ray apparatus according to claim 3, wherein the secondary target comprises Mo.

16. The x-ray apparatus according to claim 1, further including a needle extending from an end region of the collimator, the needle provided with a semi-transparent plate at a tip region thereof, one of the optically transparent paddles being provided with a hole that allows placement of the needle in a desired position to receive an optimal image of an area to be investigated.

17. The x-ray apparatus according to claim 16, wherein the thin plate is a pseudo-target that is less than 50 microns.

18. The x-ray apparatus according to claim 17, wherein the plate comprises Mo.

19. The x-ray apparatus according to claim 3, wherein a top paddle of an optically transparent panel has at least one aperture in order to allow irradiation of the anatomical site to be examined by the x-rays emanating from the focal spot of the pseudo-target placed inside a site of interest.

20. The x-ray apparatus as claimed in claim 1, wherein said apparatus comprises a gantry for computed tomography.

* * * * *